(12) United States Patent
Yamaguchi et al.

(10) Patent No.: US 7,632,608 B2
(45) Date of Patent: Dec. 15, 2009

(54) IONIC COMPOUND, ELECTROLYTIC SOLUTION, ELECTROCHEMICAL DEVICE AND BATTERY

(75) Inventors: Hiroyuki Yamaguchi, Fukushima (JP); Masayuki Ihara, Fukushima (JP); Tadahiko Kubota, Kanagawa (JP)

(73) Assignee: Sony Corporation, Tokyo (JP)

( * ) Notice: Subject to any disclaimer, the term of this patent is extended or adjusted under 35 U.S.C. 154(b) by 387 days.

(21) Appl. No.: 11/754,571

(22) Filed: May 29, 2007

(65) Prior Publication Data

US 2007/0292766 A1    Dec. 20, 2007

(30) Foreign Application Priority Data

Jun. 14, 2006    (JP)    .......................... P2006-164730

(51) Int. Cl.
     *C07C 315/00*    (2006.01)
(52) U.S. Cl. .......................... 429/324; 568/28; 570/124
(58) Field of Classification Search ................. 429/324; 568/28; 570/124
See application file for complete search history.

(56) References Cited

FOREIGN PATENT DOCUMENTS

| JP | 2002-110235 | 4/2002 |
|---|---|---|
| JP | 2005-317446 | 11/2005 |

OTHER PUBLICATIONS

Japanese Office Action dated Jun. 10, 2008 for Application No. 2006-164730.
Burford, Neil, et. al., "Preparation and Characterization of Fluoro9pentane-2,4-dionato) (trifluoromethyl) phosphorus(V) Derivatives" American Chemical Society, p. 650-657, Jul. 17, 1986.

*Primary Examiner*—Jane Rhee
(74) *Attorney, Agent, or Firm*—Sonnenschein Nath & Rosenthal LLP

(57) ABSTRACT

A battery capable of improving cycle characteristics is provided. An electrolytic solution impregnated with a separator includes an ionic compound with an asymmetric structure such as fluorotrifluoromethyl[oxalage-O,O'] lithium borate as an electrolyte salt. Thereby, compared to the case where an ionic compound with a symmetric structure such as bis[oxalate-O,O'] lithium borate or difluoro[oxalate-O,O']lithium borate is included as an electrolyte salt, the conductivity of the electrolytic solution is improved.

5 Claims, 4 Drawing Sheets

IONIC COMPOUND, ELECTROLYTIC SOLUTION, ELECTROCHEMICAL DEVICE AND BATTERY

CROSS REFERENCES TO RELATED APPLICATIONS

The present invention contains subject matter related to Japanese Patent Application JP 2006-164730 filed in the Japanese Patent Office on Jun. 14, 2006, the entire contents of which being incorporated herein by reference.

BACKGROUND OF THE INVENTION

1. Field of the Invention

The present invention relates to an ionic compound, an electrolytic solution using the same, and an electrochemical device and a battery using the same.

2. Description of the Related Art

Ionic compounds have been widely used hitherto in various fields. As an example, in the field of electrochemical devices, with emphasis on solubility, ionic dissociation and the like, an ionic compound including an anion such as $PF_6^-$ or $BF_4^-$ is used as an electrolyte salt.

In the electrochemical devices, in the field of batteries mainly used as power sources for electronic devices, specifically chargeable/dischargeable secondary batteries, research and development aimed at improving battery characteristics such as capacity characteristics or cycle characteristics have been actively conducted. Among them, secondary batteries using insertion and extraction of lithium ions for charge-discharge reaction (that is, so-called lithium-ion secondary batteries), secondary batteries using precipitation and dissolution of lithium metal (that is, so-called lithium metal secondary batteries) can obtain a large energy density, compared to lead-acid batteries or nickel-cadmium batteries in related arts, so they hold great promise.

In secondary batteries of this kind, with emphasis of a conductive property, potential stability and the like, an electrolytic solution formed by dissolving an electrolyte salt such as $LiPF_6$ in a carbonate-based nonaqueous solvent such as propylene carbonate or diethyl carbonate is widely used. As the electrolyte salt, $LiBF_4$, $LiCF_3SO_3$, $LiClO_4$, $LiAsF_6$, $LiN(CF_3SO_2)_2$, $LiN(C_2F_5SO_2)_2$, $LiN(C_4F_9SO_2)(CF_3SO_2)$ and the like are used in addition to $LiPF_6$. Moreover, recently, bis[oxalate-O,O'] lithium borate, difluoro[oxalate-O,O'] lithium borate or the like is used. The use of difluoro[oxalate-O,O'] lithium borate in the field of electrochemical devices has been proposed to improve heat resistance, hydrolysis resistance and the like (for example, refer to Japanese Unexamined Patent Application Publication No. 2002-110235).

SUMMARY OF THE INVENTION

However, ionic compounds in related arts do not have sufficient solubility and chemical stability. Therefore, in electrolytic solutions and electrochemical devices using the ionic compounds in related arts, there is a limit to various performance capabilities. More specifically, it is difficult for the electrolytic solutions to obtain sufficient conductivity, and it is difficult for secondary batteries to obtain sufficient cycle characteristics.

In view of the foregoing, it is desirable to provide an ionic compound capable of improving solubility and chemical stability.

Moreover, it is desirable to provide an electrolytic solution capable of improving conductivity.

Further, it is desirable to provide an electrochemical device and a battery capable of improving cycle characteristics.

According to an embodiment of the invention, there is provided an ionic compound including: a structure shown in Chemical Formula 1:

[Chemical Formula 1]

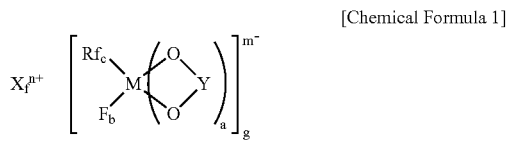

where $X^{n+}$ represents an ion of a Group 1A element or a Group 2A element in the short form of the periodic table of the elements, or an onium ion, M represents a transition metal, or a Group 3B element, a Group 4B element or a Group 5B element in the short form of the periodic table of the elements, Rf represents a fluorinated alkyl group or a fluorinated aryl group having a carbon number of 1 to 10, and Y represents $ZC(CR_2)_dCZ$, $O_2S(CR_2)_eSO_2$ or $OC(CR_2)_eSO_2$ (Z represents =O, a halogenated alkyl group or a halogen group, R represents a hydrogen group, an alkyl group, a halogenated alkyl group or a halogen group), and a, g and n each are an integer of 1 or 2, b, c and e each are an integer of 1 to 4, d is 0 or an integer of 1 to 4, and f and m each are an integer of 1 to 3.

According to an embodiment of the invention, there is provided an electrolytic solution including: a solvent and an electrolyte salt shown in Chemical Formula 2:

[Chemical Formula 2]

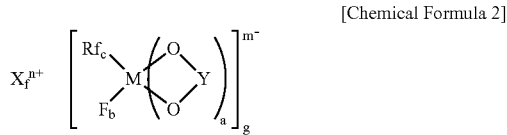

where $X^{n+}$ represents an ion of a Group 1A element or a Group 2A element in the short form of the periodic table of the elements, or an onium ion, M represents a transition metal, or a Group 3B element, a Group 4B element or a Group 5B element in the short form of the periodic table of the elements, Rf represents a fluorinated alkyl group or a fluorinated aryl group having a carbon number of 1 to 10, and Y represents $ZC(CR_2)_dCZ$, $O_2S(CR_2)_eSO_2$ or $OC(CR_2)_eSO_2$ (Z represents =O, a halogenated alkyl group or a halogen group, R represents a hydrogen group, an alkyl group, a halogenated alkyl group or a halogen group), and a, g and n each are an integer of 1 or 2, b, c and e each are an integer of 1 to 4, d is 0 or an integer of 1 to 4, and f and m each are an integer of 1 to 3.

According to an embodiment of the invention, there is provided an electrochemical device including: an electrolytic solution including an electrolyte salt shown in Chemical Formula 3:

[Chemical Formula 3]

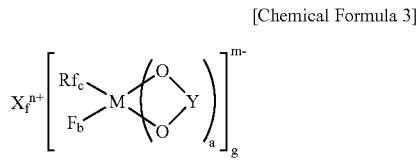

where $X^{n+}$ represents an ion of a Group 1A element or a Group 2A element in the short form of the periodic table of the elements, or an onium ion, M represents a transition metal, or a Group 3B element, a Group 4B element or a Group 5B element in the short form of the periodic table of the elements, Rf represents a fluorinated alkyl group or a fluorinated aryl group having a carbon number of 1 to 10, and Y represents $ZC(CR_2)_dCZ$, $O_2S(CR_2)_eSO_2$ or $OC(CR_2)_eSO_2$ (Z represents =O, a halogenated alkyl group or a halogen group, R represents a hydrogen group, an alkyl group, a halogenated alkyl group or a halogen group), and a, g and n each are an integer of 1 or 2, b, c and e each are an integer of 1 to 4, d is 0 or an integer of 1 to 4, and f and m each are an integer of 1 to 3.

According to an embodiment of the invention, there is provided a battery including: a cathode, an anode and an electrolytic solution, wherein the electrolytic solution includes an electrolyte salt shown in Chemical Formula 4:

[Chemical Formula 4]

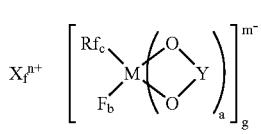

where $X^{n+}$ represents an ion of a Group 1A element or a Group 2A element in the short form of the periodic table of the elements, or an onium ion, M represents a transition metal, or a Group 3B element, a Group 4B element or a Group 5B element in the short form of the periodic table of the elements, Rf represents a fluorinated alkyl group or a fluorinated aryl group having a carbon number of 1 to 10, and Y represents $ZC(CR_2)_dCZ$, $O_2S(CR_2)_eSO_2$ or $OC(CR_2)_eSO_2$ (Z represents =O, a halogenated alkyl group or a halogen group, R represents a hydrogen group, an alkyl group, a halogenated alkyl group or a halogen group), and a, g and n each are an integer of 1 or 2, b, c and e each are an integer of 1 to 4, d is 0 or an integer of 1 to 4, and f and m each are an integer of 1 to 3.

In the ionic compound according to the embodiment of the invention, the structure shown in Chemical Formula 1 is included, so solubility and chemical stability can be improved. Therefore, in the electrolytic solution according to the embodiment of the invention which uses the ionic compound, conductivity can be improved. Moreover, in the electrochemical device and the battery according to the embodiment of the invention which use the electrolytic solution, cycle characteristics can be improved.

Other and further objects, features and advantages of the invention will appear more fully from the following description.

DETAILED DESCRIPTION OF THE PREFERRED EMBODIMENTS

Figure 1:
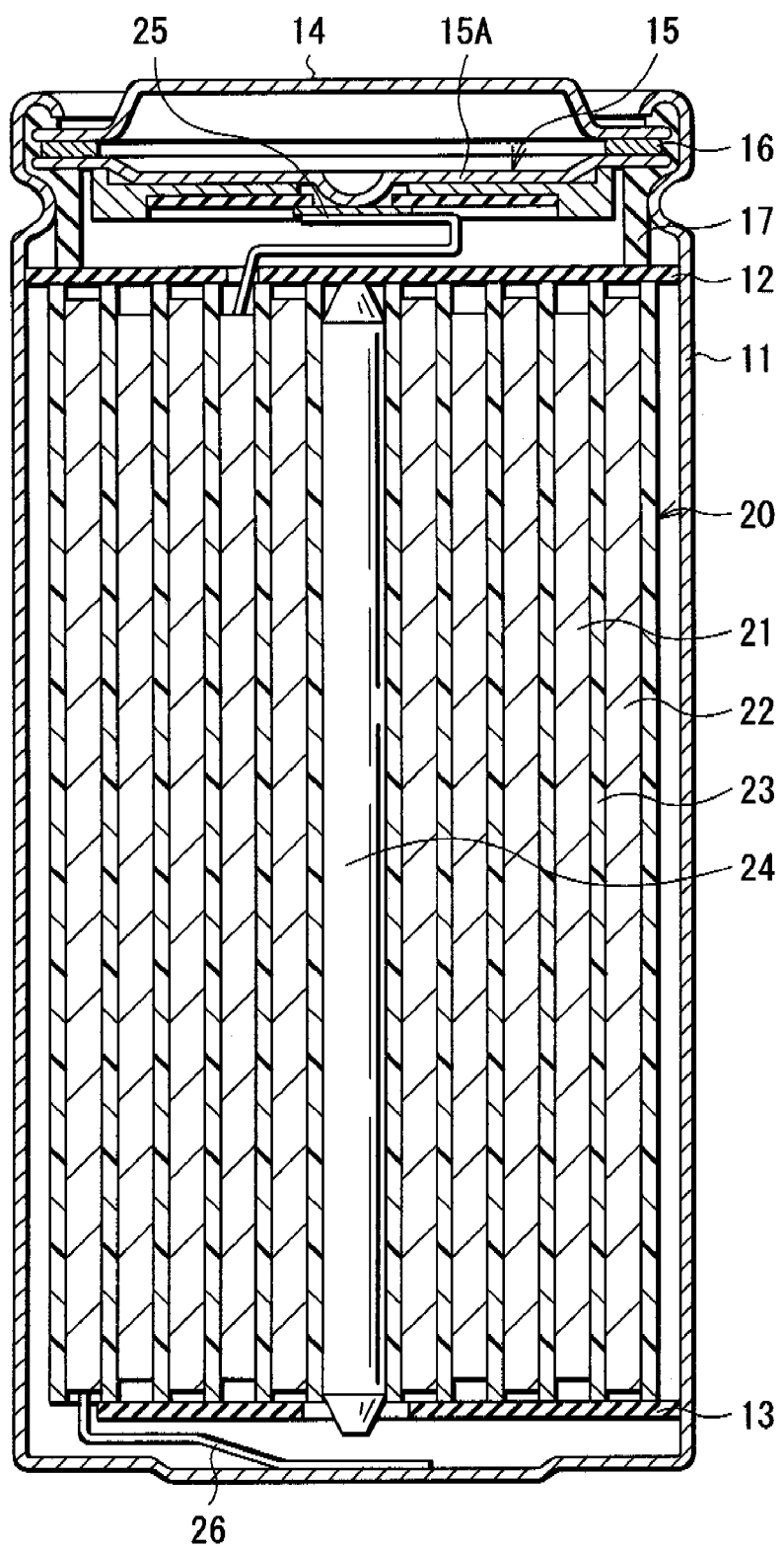
FIG. 1 shows a sectional view of a first battery using an ionic compound according to an embodiment of the invention as an electrolyte salt.

A preferred embodiment will be described in detail below referring to the accompanying drawings.

An ionic compound according to an embodiment of the invention has a structure shown in Chemical Formula 5. The ionic compound includes an anion in which three different kinds of groups, that is, a fluorine group (—F), a fluorinated alkyl group or fluorinated aryl group (—Rf), and a ligand (—O—Y—O—) having an oxygen chelate structure are introduced into a central element (M).

[Chemical Formula 5]

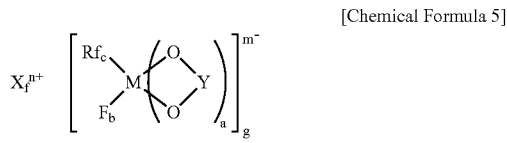

where $X^{n+}$ represents an ion of a Group 1A element or a Group 2A element in the short form of the periodic table of the elements, or an onium ion, M represents a transition metal, or a Group 3B element, a Group 4B element or a Group 5B element in the short form of the periodic table of the elements, Rf represents a fluorinated alkyl group or a fluorinated aryl group having a carbon number of 1 to 10, and Y represents $ZC(CR_2)_dCZ$, $O_2S(CR2)_eSO_2$ or $OC(CR_2)_eSO_2$ (Z represents =O, a halogenated alkyl group or a halogen group, R represents a hydrogen group, an alkyl group, a halogenated alkyl group or a halogen group), and a, g and n each are an integer of 1 or 2, b, c and e each are an integer of 1 to 4, d is 0 or an integer of 1 to 4, and f and m each are an integer of 1 to 3.

Examples of the ionic compound classified by kinds of cations are as follows.

Ionic compounds including a lithium ion ($Li^+$) as a representative of the ion of the Group 1A element or the Group 2A element include a series of compounds shown in Chemical Formula 6, that is, fluorotrifluoromethyl[oxalate-O,O'] lithium borate in Chemical Formula 6(1), fluoropentafluoroethyl[oxalate-O,O'] lithium borate in Chemical Formula 6(2), fluorotrifluoromethyl[malonate-O,O'] lithium borate in Chemical Formula 6(3), fluorotrifluoromethyl[difluoromalonate-O,O']lithium borate in Chemical Formula 6(4), fluorotrifluoromethyl[3,3,3-trifluoro-2-oxide-2-trifluoromethyl-propionate(2-)—O,O'] lithium borate in Chemical Formula 6(5), fluorotrispentafluoroethyl[oxalate-O,O'] lithium phosphate in Chemical Formula 6(6), fluorotrispentafluoroethyl[malonate-O,O'] lithium phosphate in Chemical Formula 6(7), fluorotrispentafluoroethyl[difluoromalonate-O,O'] lithium phosphate in Chemical Formula 6(8), fluorotrifluoromethyl[methylenedisulfonate-O,O']lithium borate in Chemical Formula 6(9), fluorotrifluoromethyl[sulfoacetate-O,O'] lithium borate in Chemical Formula 6(10) and the like.

[Chemical Formula 6]

(1)

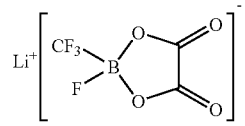

-continued (2) 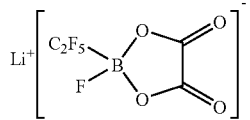

(3) 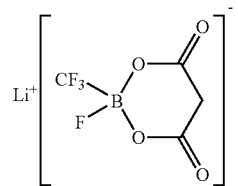

(4) 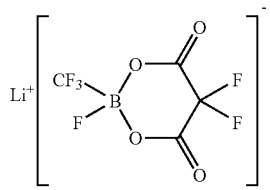

(5) 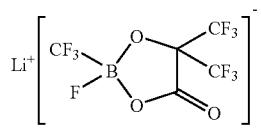

(6) 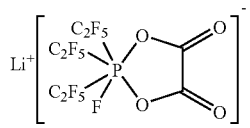

(7) 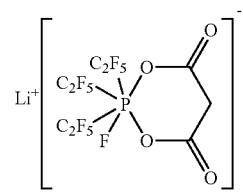

(8) 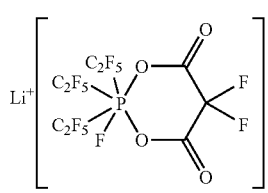

(9) 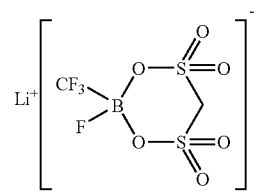

-continued

(10) 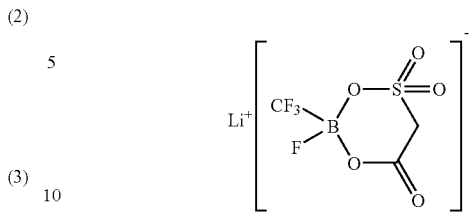

Ionic compounds including a tetraethylammonium ion $((C_2H_5)_4N^+)$ as a representative of the onium ion include a series of compounds shown in Chemical Formula 7, that is, fluorotrifluoromethyl[oxalate-O,O']tetraethylammonium borate in Chemical Formula 7(1), fluoropentafluoroethyl[oxalate-O,O'] tetraethylammonium borate in Chemical Formula 7(2), fluorotrifluoromethyl[malonate-O,O']tetraethylammonium borate in Chemical Formula 7(3), fluorotrifluoromethyl [difluoromalonate-O,O'] tetraethylammonium borate in Chemical Formula 7(4), fluororomethyl[3,3,3-trifluoro-2-oxide-2-trifluoromethylpropionate(2-)—O,O'] traethylammonium borate in Chemical Formula 7(5), flurotrispentafluoroethyl[oxalate-O,O']tetraethylammonium phosphate in Chemical Formula 7(6), fluorotrispentagluoroethyl] [malonate-O,O'] tetraethylammonium phosphate in Chemical Formula 7(7), fluorotrispentafluoroethyl[difluoromalonate-O,O'] tetraethylammonium phosphate in Chemical Formula 7(8), fluorotrifluoromethyl] [methylenedisulfonate-O,O'] tetraethylammonium borate in Chemical Formula 7(9), fluorotrifluoromethyl[sulfoacetate-O,O']tetraethylammonium borate in Chemical Formula 7(10) and the like.

[Chemical Formula 7]

(1) 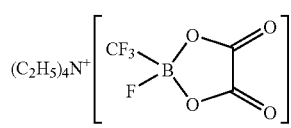

(2) 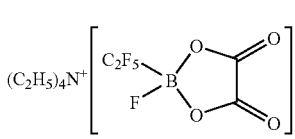

(3) 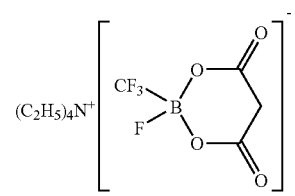

(4) 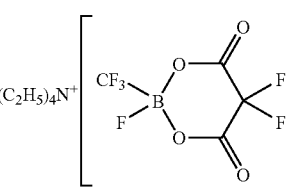

-continued (5) 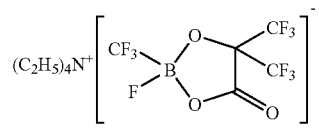

(6) 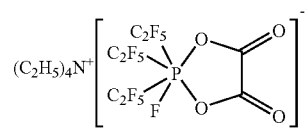

(7) 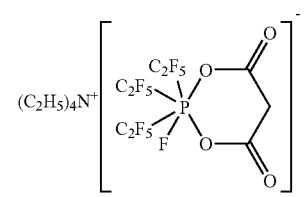

(8) 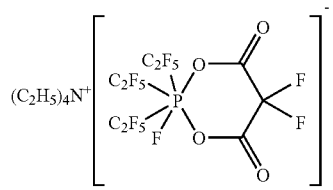

(9) 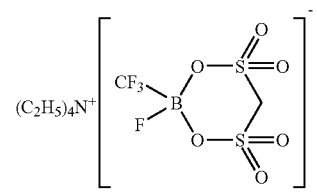

(10) 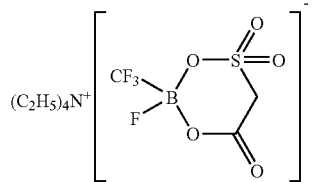

Ionic compounds including a triethylmethylammonium ion ($(C_2H_5)_3NCH_{3+}$) include a series of compounds shown in Chemical Formula 8, that is, fluorotrifluoromethyl[oxalate-O,O'] triethylmethylammonium borate in Chemical Formula 8(1), fluoropentafluoroethyl[oxalate-O,O']triethylmethylammonium borate in Chemical Formula 8(2), fluorotrifluoromethyl[malonate-O,O'] triethylmethylammonium borate in Chemical Formula 8(3), fluorotrifluoromethyl[difluoromalonate-O,O']triethylmethylammonium borate in Chemical Formula 8(4), fluorotrifluoromethyl[3,3,3-trifluoro-2-oxide-2-trifluoromethylpropionate(2-)—O,O'] triethylmethylammonium borate in Chemical Formula 8(5), fluorotrispentafluoroethyl] [oxalate-O,O'] triethylmethylammonium phosphate in Chemical Formula 8(6), fluorotrispentafluoroethyl[malonate-O,O'] triethylmethylammonium phosphate in Chemical Formula 8(7), fluorotrispentafluoroethyl[difluoromalonate-O,O']triethylmethylammonium phosphate in Chemical Formula 8(8), fluorotrifluoromethyl[methylenedisulfonate-O,O']triethylmethylammonium borate in Chemical Formula 8(9), fluorotrifluoromethyl[sulfoacetate-O,O'] triethylmethylammonium borate in Chemical Formula 8(10) and the like.

[Chemical Formula 8]

(1) 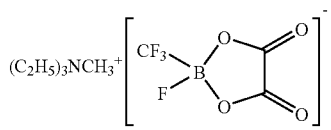

(2) 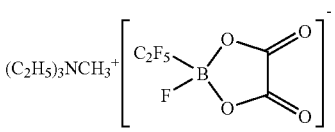

(3) 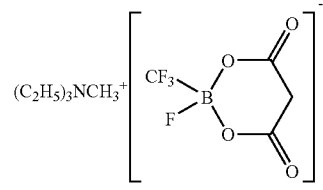

(4) 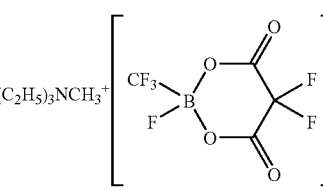

(5) 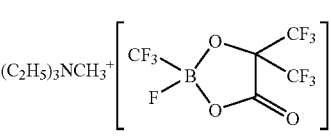

(6) 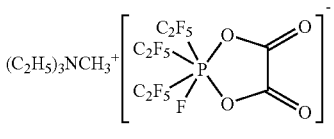

(7) 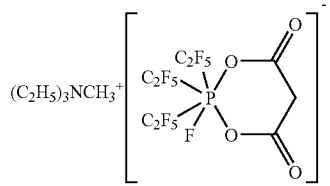

(8) 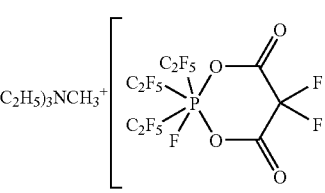

-continued (9)
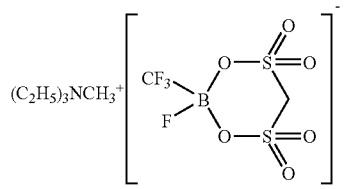

(10)
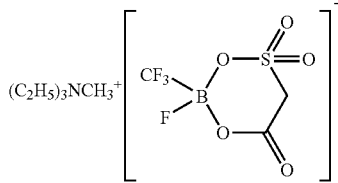

Ionic compounds including an ethylmethylimidazolium ion ($C_6H_{11}N_{2+}$) include a series of compounds shown in Chemical Formula 9, that is, fluorotrifluoromethyl[oxalate-O,O'] ethylmethylimidazolium borate in Chemical Formula 9(1), fluoropentafluoroethyl[oxalate-O,O']ethylmethylimidazolium borate in Chemical Formula 9(2), fluorotrifluoromethyl[malonate-O,O'] ethylmethylimidazolium borate in Chemical Formula 9(3), fluorotrifluoromethyl[difluoromalonate-O,O']ethylmethylimidazolium borate in Chemical Formula 9(4), fluorotrifluoromethyl[3,3,3-trifluoro-2-oxide-2-trifluoromethylpropionate(2-)—O,O'] ethylmethylimidazolium borate in Chemical Formula 9(5), fluorotrispentafluoroethyl] [oxalate-O,O'] ethylmethylimidazolium phosphate in Chemical Formula 9(6), fluorotrispentafluoroethyl[malonate-O,O'] ethylmethylimidazolium phosphate in Chemical Formula 9(7), fluorotrispentafluoroethyl [difluoromalonate-O,O'] ethylmethylimidazolium phosphate in Chemical Formula 9(8), fluorotrifluoromethyl[methylenedisulfonate-O,O'] ethylmethylimidazolium borate in Chemical Formula 9(9), fluorotrifluoromethyl[sulfoacetate-O,O']ethylmethylimidazolium borate in Chemical Formula 9(10) and the like.

[Chemical Formula 9]

(1)
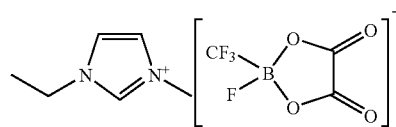

(2)
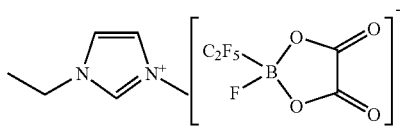

(3)
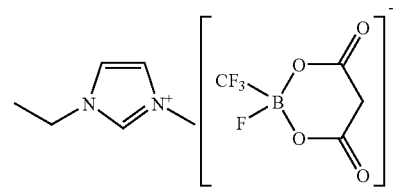

(4)
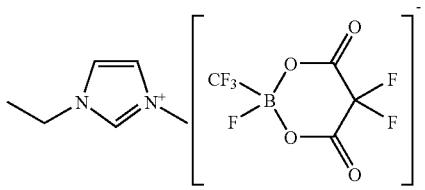

(5)
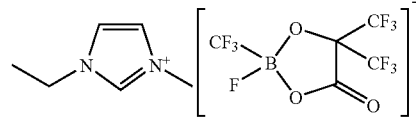

(6)
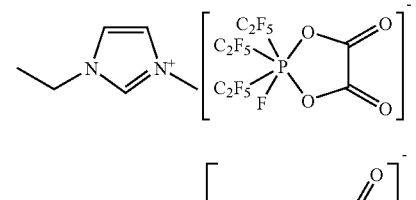

(7)
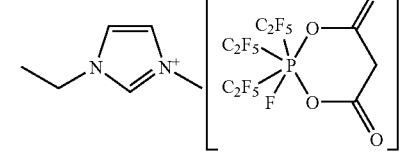

(8)
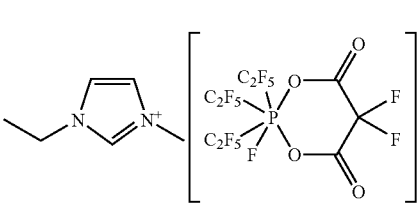

(9)
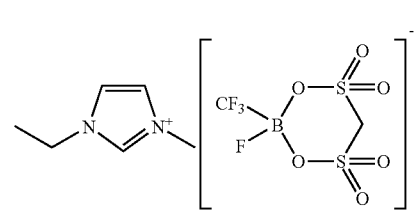

(10)
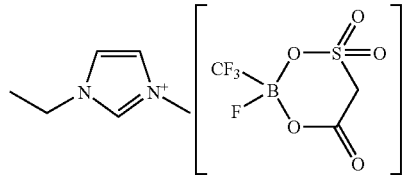

As long as the ionic compound has the structure shown in Chemical Formula 5, the ionic compound is not limited to the compounds shown in Chemical Formulas 6 to 9. Examples of the cation include an ammonium ion ($NH_{4+}$), a phosphonium ion ($PH_{4+}$) and the like in addition to the above-described cations, although they are not described in detail here.

In the ionic compound, the anion has an asymmetric structure in which three different types of groups are introduced into a central element, so compared to the case where the anion has a symmetric structure, the following advantages can be obtained. Firstly, dissociation is improved by the high electron-withdrawing property of the fluorine group. Secondly, dissociation is improved by the high electron-withdrawing property of the fluorinated alkyl group or the fluorinated aryl group, and the central element has resistance to reacting by their large spatial sizes (spatial protection effects), that is, decomposition is prevented. Thirdly, decomposition is prevented by the large spatial size of the ligant having an oxygen chelate structure.

The ionic compound may be used singly, or in combination with another material. Moreover, the application of the ionic compound can be freely set, for example, according to the kind of cation. As an example, an ionic compound including an asymmetric ammonium ion such as triethylmethylammonium ion or an imidazolium ion can be used singly as an ionic liquid. Further, an ionic compound including a lithium ion, an ammonium ion, a phosphonium ion or the like can be used in an electrochemical device as an electrolyte salt included in an electrolytic solution. In particular, an ionic compound including a lithium ion is suitable for secondary batteries, and an ionic compound including an ammonium ion and a phosphonium ion is suitable for electric double layer capacitors and the like.

The ionic compound has the structure shown in Chemical Formula 5, so as described above, dissociation is improved, and decomposition is prevented. Therefore, solubility and chemical stability can be improved.

Next, examples of use of the ionic compound according to the embodiment will be described below. In the case where a secondary battery including an electrolytic solution is cited as an example of an electrochemical device, the ionic compound is used in the secondary battery in the following manner.

(First Battery)

FIG. 1 shows a sectional view of a first battery using the ionic compound as an electrolyte salt. In this battery, the capacity of an anode is represented by a capacity component based on insertion and extraction of lithium as an electrode reactant, and the battery is a so-called a lithium-ion secondary battery. FIG. 1 shows a battery structure called a so-called cylindrical type, and the battery includes a spirally wound electrode body 20 which includes a cathode 21 and an anode 22 spirally wound with a separator 23 in between and a pair of insulating plates 12 and 13 in a substantially hollow cylindrical-shaped battery can 11. The battery can 11 is made of, for example, nickel (Ni)-plated iron (Fe). An end portion of the battery can 11 is closed, and the other end portion thereof is opened. The pair of insulating plates 12 and 13 are arranged so that the spirally wound electrode body 20 is sandwiched therebetween in a direction perpendicular to a peripheral winding surface.

In the opened end portion of the battery can 11, a battery cover 14, and a safety valve mechanism 15 and a positive temperature coefficient device (PTC device) 16 arranged inside the battery cover 14 are mounted by caulking by a gasket 17, and the interior of the battery can 11 is sealed. The battery cover 14 is made of, for example, the same material as that of the battery can 11. The safety valve mechanism 15 is electrically connected to the battery cover 14 through the PTC device 16, and in the safety valve mechanism 15, when an internal pressure in the battery increases to a certain extent or higher due to an internal short circuit or external application of heat, a disk plate 15A is flipped so as to disconnect the electrical connection between the battery cover 14 and the spirally wound electrode body 20. When a temperature rises, the PTC device 16 limits a current by an increased resistance to prevent abnormal heat generation by a large current. The gasket 17 is made of, for example, an insulating material, and its surface is coated with asphalt.

A center pin 24 is inserted into the center of the spirally wound electrode body 20. In the spirally wound electrode body 20, a cathode lead 25 made of aluminum (Al) or the like is connected to the cathode 21, and an anode lead 26 made of nickel or the like is connected to the anode 22. The cathode lead 25 is welded to the safety valve mechanism 15 so as to be electrically connected to the battery cover 14, and the anode lead 26 is welded to the battery can 11 so as to be electrically connected to the battery can 11.

Figure 2:
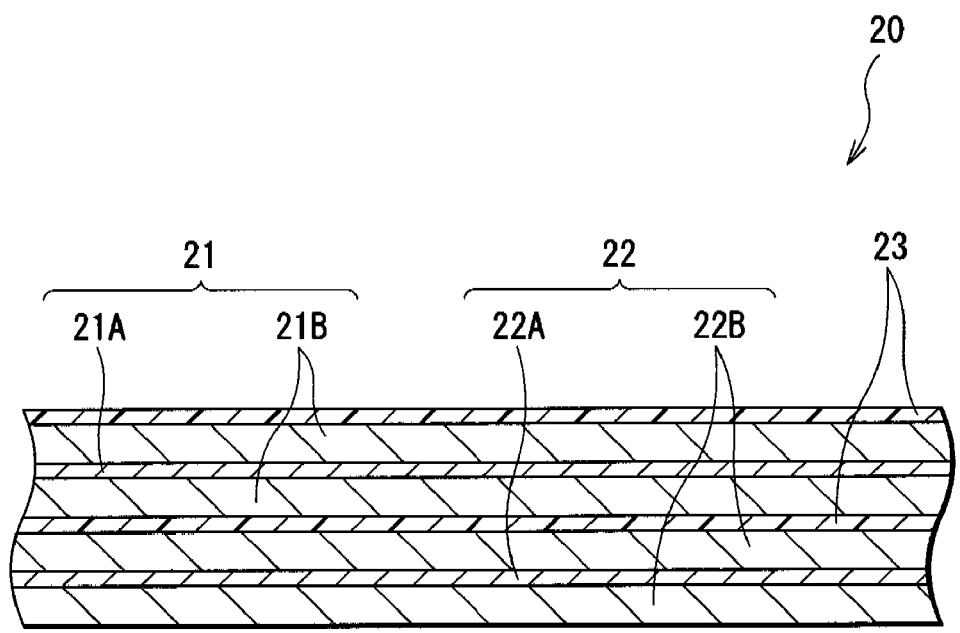
FIG. 2 is an enlarged sectional view of a part of a spirally wound electrode body shown in FIG. 1.

FIG. 2 shows an enlarged view of a part of the spirally wound electrode body 20 shown in FIG. 1. The cathode 21 is formed by arranging a cathode active material layer 21B on both sides of a cathode current collector 21A having a pair of facing surfaces. The cathode current collector 21A is made of, for example, a metal material such as aluminum, nickel or stainless. The cathode active material layer 21B includes one kind or two or more kinds of cathode materials capable of inserting and extracting lithium as electrode reactants. The cathode active material layer 21B may include an electrical conductor such as a carbon material and a binder such as polyvinylidene fluoride, if necessary.

As the cathode material capable of inserting and extracting lithium, for example, lithium cobalt oxide, lithium nickel oxide, a solid solution including lithium cobalt oxide and lithium nickel oxide ($Li(Ni_xCo_yMn_z)O_2$)) (the values of x, y and z are $0<x<1$, $0<y<1$ and $0<z<1$, and $x+y+z=1$), lithium complex oxide such as lithium manganese oxide ($LiMn_2O_4$) with a spinel structure or a solid solution thereof ($Li(Mn_{2-v}Ni_v)O_4$) (the value of v is $v<2$), or a phosphate compound with an olivine structure such as lithium iron phosphate ($LiFePO_4$) is preferable, because a high energy density can be obtained. Moreover, Examples of the cathode material capable of inserting and extracting lithium include oxides such as titanium oxide, vanadium oxide and manganese dioxide, bisulfides such as iron bisulfide, titanium bisulfide and molybdenum sulfide, sulfur, and conductive polymers such as polyaniline and polythiophene.

The anode 22 is formed by arranging an anode active material layer 22B on both sides of an anode current collector 22A having a pair of facing surfaces. The anode current collector 22A is made of, for example, a metal material such as copper (Cu), nickel or stainless. The anode active material layer 22B includes one kind or two or more kinds of anode materials capable of inserting and extracting lithium. The anode active material layer 22B may include an electrical conductor, a binder or the like if necessary.

As the anode material capable of inserting and extracting lithium, for example, a material which can insert and extract lithium and includes at least one kind selected from the group consisting of metal elements and metalloid elements as an element is cited. Such an anode material is preferably used, because a high energy density can be obtained. The anode material may include the simple substance, an alloy or a compound of a metal element or a metalloid element, and may include a phase of one kind or two or more kinds selected from them at least in part. In the invention, the alloy includes an alloy including one or more kinds of metal elements and one or more kinds of metalloid elements in addition to an alloy including two or more kinds of metal elements. Further, the alloy may include a non-metal element. As the texture of the alloy, a solid solution, a eutectic (eutectic mixture), an intermetallic compound or the coexistence of two or more kinds selected from them is cited.

Examples of the metal elements or the metalloid elements included in the anode material include metal elements and metalloid elements capable of forming an alloy with lithium. More specifically, magnesium (Mg), boron (B), aluminum, gallium (Ga), indium (In), silicon, germanium (Ge), tin, lead (Pb), bismuth (Bi), cadmium (Cd), silver (Ag), zinc (Zn), hafnium (Hf), zirconium (Zr), yttrium (Y), palladium (Pd), platinum (Pt) or the like is included. Among them, silicon or tin is specifically preferable, because silicon and tin have a large capability to insert and extract lithium, so a high energy density can be obtained.

As such an anode material, for example, an anode material including tin as a first element, a second element and a third element is preferable. The second element includes at least one kind selected from the group consisting of cobalt (Co), iron, magnesium, titanium (Ti), vanadium (V), chromium (Cr), manganese (Mn), nickel, copper, zinc, gallium, zirconium, niobium (Nb), molybdenum (Mo), silver, indium, cerium (Ce), hafnium, tantalum (Ta), tungsten (W), bismuth and silicon. The third element includes at least one kind selected from the group consisting of boron, carbon (C), aluminum and phosphorus (P). When the second element and the third element are included, cycle characteristics can be improved.

Among them, as the anode material, a CoSnC-containing material in which tin, cobalt and carbon are included as elements, and the carbon content is within a range from 9.9 wt % to 29.7 wt % inclusive, and the ratio of cobalt to the total of tin and cobalt (Co/(Sn+Co)) is within a range from 30 wt % to 70 wt % inclusive is preferable, because a high energy density and superior cycle characteristics can be obtained in such a composition range.

The CoSnC-containing material may include any other element, if necessary. As the element, for example, silicon, iron, nickel, chromium, indium, niobium, germanium, titanium, molybdenum, aluminum, phosphorus, gallium or bismuth is preferable, and two or more kinds selected from them may be included. It is because the capacity or the cycle characteristics can be further improved.

The CoSnC-containing material includes a phase including tin, cobalt and carbon, and the phase preferably has a low crystalline structure or an amorphous structure. Moreover, in the CoSnC-containing material, at least a part of carbon as an element is preferably bonded to a metal element or a metalloid element as another element. It is considered that a decline in the cycle characteristics is caused by cohesion or crystallization of tin or the like, and when carbon is bonded to another element, such cohesion or crystallization can be prevented.

As a measuring method for checking the bonding state of an element, for example, X-ray photoelectron spectroscopy (XPS) is used. In the XPS, the peak of the 1s orbit (C1s) of carbon in the case of graphite is observed at 284.5 eV in an apparatus in which energy calibration is performed so that the peak of the 4f orbit (Au4f) of a gold atom is observed at 84.0 eV. Moreover, the peak of C1s of the surface contamination carbon is observed at 284.8 eV. On the other hand, in the case where the charge density of the carbon element increases, for example, in the case where carbon is bonded to a metal element or a metalloid element, the peak of C1s is observed in a region lower than 284.5 eV. In other words, in the case where the peak of the composite wave of C1s obtained in the CoSnC-containing material is observed in a region lower than 284.5 eV, at least a part of carbon included in the CoSnC-containing material is bonded to the metal element or the metalloid element which is another element.

Moreover, in the XPS measurement, for example, the peak of C1s is used to correct the energy axis of a spectrum. In general, surface contamination carbon exists on a material surface, so the peak of C1s of the surface contamination carbon is fixed at 284.8 eV, and the peak is used as an energy reference. In the XPS measurement, the waveform of the peak of C1s is obtained as a form including the peak of the surface contamination carbon and the peak of carbon in the CoSnC-containing material, so the peak of the surface contamination carbon and the peak of the carbon in the CoSnC-containing material are separated by analyzing the waveform through the use of, for example, commercially available software. In the analysis of the waveform, the position of a main peak existing on a lowest binding energy side is used as an energy reference (284.8 eV).

As the anode material capable of inserting and extracting lithium, for example, a carbon material such as graphite, non-graphitizable carbon or graphitizable carbon is used. The carbon material and the above-described anode material may be used together. In the carbon material, a change in crystal structure according to insertion and extraction of lithium is very small, so the carbon material is preferably used together with the above-described anode material, because a high energy density and superior cycle characteristics can be obtained, and the carbon material also functions as an electrical conductor.

In the secondary battery, the amounts of the cathode active material and the anode material capable of inserting and extracting lithium are adjusted so that a charge capacity by the anode material capable of inserting and extracting lithium becomes larger than a charge capacity by the cathode active material, thereby lithium metal is not precipitated on the anode 22 even at the time of full charge.

The separator 23 isolates between the cathode 21 and the anode 22 so that lithium ions pass therethrough while preventing a short circuit of a current due to contact between the cathode 21 and the anode 22. The separator 23 is made of, for example, a porous film of a synthetic resin such as polytetrafluoroethylene, polypropylene or polyethylene, or a porous ceramic film, and the separator 23 may have a structure in which two or more kinds of the porous films are laminated.

The separator 23 is impregnated with an electrolytic solution as a liquid electrolyte. The electrolytic solution includes a liquid solvent, for example, a nonaqueous solvent such as an organic solvent, and an electrolyte salt dissolved in the nonaqueous solvent.

Examples of the nonaqueous solvent include ethylene carbonate, propylene carbonate, butylene carbonate, vinylene carbonate, 1,3-dioxol-2-one, 4-vinyl-1,3-dioxolane-2-one, dimethyl carbonate, diethyl carbonate, ethyl methyl carbonate, methyl propyl carbonate, γ-butyrolactone, γ-valerolactone, 1,2-dimethoxyethane, tetrahydrofuran, 2-methyltetrahydrofuran, tetrahydropyran, 1,3-dioxolane, 4-methyl-1,3-dioxolane, 1,3-dioxane, 1,4-dioxane, methyl acetate, ethyl acetate, methyl propionate, ethyl propionate, methyl butyrate, methyl isobutyrate, methyl trimethylacetate, ethyl trimethylacetate, acetonitrile, glutaronitrile, adiponitrile, methoxyacetonitrile, 3-methoxypropionitrile, N,N-dimethylformamide, N-methylpyrrolidinone, N-methyloxazolidinone, N,N'-dimethylimidazolidinone, nitromethane, nitroethane, sulfolane, dimethyl sulfoxide phosphate and the like. One kind or a mixture including two or more kinds selected from these nonaqueous solvent may be used. Among them, at least one kind selected from the group consisting of ethylene carbonate, propylene carbonate, vinylene carbonate, dimethyl carbonate and ethyl methyl carbonate is preferably used, because superior charge-discharge capacity characteristics and charge-discharge cycle characteristics can be obtained.

The electrolyte salt includes the ionic compound according to the embodiment, because the ionic compound improves the conductive property and the chemical stability of the electrolytic solution, so the cycle characteristics can be improved.

The electrolyte salt may include one kind or two or more kinds of light metal salts (except for light metal salts coinciding with ionic compounds). It is because the electrochemical property of the electrolytic solution can be improved. Examples of the light metal salt include $LiB(C_6H_5)_4$, $LiCH_3SO_3$, $LiCF_3SO_3$, $LiAlCl_4$, $LiSiF_6$, $LiCl$, $LiBr$, $LiPF_6$, $LiBF_4$, $LiB(OCOCF_3)_4$, $LiB(OCOC_2F_5)_4$, $LiClO_4$, $LiAsF_6$, $LiN(CF_3SO_2)_2$, $LiN(C_2H_5SO_2)_2$, $LiN(C_4F_9SO_2)(CF_3SO_2)$, lithium cyclic 1,2-perfluoroethanedisulfonylimide, 1,3-perfluoropropanedisulfonylimide, lithium cyclic 1,3-perfluorobutanedisulfonylimide, lithium cyclic 1,4-perfluorobutanedisulfonylimide, lithium cyclic perfluoroheptane diol imide and the like. One kind or a mixture of a plurality of kinds of these electrolyte salts may be used. Among them, at least one kind selected from the group consisting of $LiPF_6$, $LiBF_4$, $LiClO_4$ and $LiAsF_6$ is preferably used, because a higher electrochemical property can be obtained, and high conductivity can be obtained. In particular, a mixture of $LiPF_6$ and at least one kind selected from the group consisting of $LiBF_4$, $LiClO_4$, $LiAsF_6$, a lithium imide salt and a cyclic lithium imide salt is preferably included, because higher effects can be obtained.

The content of the electrolyte salt in a solvent is preferably within a range from 0.3 mol/kg to 3.0 mol/kg inclusive. It is because when the content of the electrolyte salt is out of the range, ionic conductivity is drastically reduced, thereby it may be difficult to obtain sufficient battery characteristics. In particular, in the case where the electrolyte salt includes a light metal salt, the content of the light metal salt in the solvent is preferably within a range from 0.01 mol/kg to 2.0 mol/kg inclusive, because higher effects can be obtained in this range.

The secondary battery can be manufactured by the following steps, for example.

At first, for example, the cathode active material layer 21B is formed on both sides of the cathode current collector 21A so as to form the cathode 21. The cathode active material layer 21B is formed by the following steps. A cathode mixture formed by mixing cathode active material powder, the electrical conductor and the binder is dispersed in a solvent such as N-methyl-2-pyrrolidone to form paste-form cathode mixture slurry, and the cathode mixture slurry is applied to the cathode current collector 21A, and the cathode mixture slurry is dried and compression molded, thereby the cathode active material layer 21B is formed. Moreover, for example, by the same steps as those in the case of the cathode 21, the anode 22 is formed by forming the anode active material layer 22B on the both sides of the anode current collector 22A.

Next, the cathode lead 25 is attached to the cathode current collector 21A by welding or the like, and the anode lead 26 is attached to the anode current collector 22A by welding or the like. Then, the cathode 21 and the anode 22 are spirally wound with the separator 23 in between so as to form the spirally wound electrode body 20, and a front end portion of the cathode lead 25 is welded to the safety valve mechanism 15, and a front end portion of the anode lead 26 is welded to the battery can 11. Next, the spirally wound electrode body 20 is sandwiched between the pair of insulating plates 12 and 13, and they are contained in the battery can 11. Next, the electrolytic solution is injected into the battery can 11 so as to impregnate the separator 23 with the electrolytic solution. Finally, the battery cover 14, the safety valve mechanism 15 and the PTC device 16 are fixed in an opened end portion of the battery can 11 by caulking by the gasket 17. Thereby, the secondary battery shown in FIGS. 1 and 2 is completed.

When the secondary battery is charged, lithium ions are extracted from the cathode 21, and are inserted into the anode 22 through the electrolytic solution. On the other hand, when the secondary battery is discharged, the lithium ions are extracted from the anode 22 and are inserted into the cathode 21 through the electrolytic solution.

In the secondary battery, in the case where the capacity of the anode is represented by a capacity component based on insertion and extraction of lithium, the ionic compound shown in Chemical Formula 5 as an electrolyte salt is included in the electrolytic solution, so in the electrolytic solution, high conductivity can be obtained. Therefore, the cycle characteristics can be improved.

(Second Battery)

A second battery has the same structure, functions and effects as those of the first battery, except for the structure of an anode 22 is different, and the second battery can be manufactured by the same method. Therefore, the second battery will be described referring to FIGS. 1 and 2, and like components are denoted by like numerals as of the first battery, and will not be further described.

The anode 22 has a structure in which the anode active material layer 22B is arranged on both sides of the anode current collector 22A as in the case of the first battery. The anode active material layer 22B includes, for example, an anode active material including tin or silicon as an element. More specifically, for example, the anode active material includes the simple substance, an alloy or a compound of tin, or the simple substance, an alloy or a compound of silicon, and the anode active material may include two or more kinds selected from them.

The anode active material layer 22B is formed by, for example, a vapor-phase method, a liquid-phase method, a spraying method or a firing method, or a combination of two or more methods selected from them, and the anode active material layer 22B and the anode current collector 22A are preferably alloyed in at least a part of an interface therebetween. More specifically, in the interface, an element of the anode current collector 22A is preferably diffused into the anode active material layer 22B, or an element of the anode active material is preferably diffused into the anode current collector 22A, or they are preferably diffused into each other, because a fracture of the anode active material layer 22B due to expansion and shrinkage thereof according to charge and discharge can be inhibited, and the electronic conductivity between the anode active material layer 22B and the anode current collector 22A can be improved.

As the vapor-phase method, for example, a physical deposition method or a chemical deposition method can be used, and more specifically, a vacuum deposition method, a sputtering method, an ion plating method, a laser ablation method, a thermal CVD (chemical vapor deposition) method, a plasma chemical vapor deposition method or the like can be used. As the liquid-phase method, a known technique such as electrolytic plating or electroless plating can be used. In the firing method, for example, a particulate anode active material is mixed with a binder or the like to form a mixture, and the mixture is dispersed in a solvent, and is applied, and then the mixture is heated at a higher temperature than the melting point of the binder or the like. As the firing method, a known technique such as, for example, an atmosphere firing method, a reaction firing method or a hot press firing method can be used.

(Third Battery)

In a third battery, the capacity of the anode 22 is represented by a capacity component based on precipitation and dissolution of lithium, and the third battery is a so-called lithium metal secondary battery. The secondary battery has the same structure as that of the first battery, except that the anode active material layer 22B is made of lithium metal, and the secondary battery can be manufactured by the same method. Therefore, the third battery will be described referring to FIGS. 1 and 2, and like components are denoted by like numerals as of the first battery, and will not be further described.

The secondary battery uses lithium metal as the anode active material, so a higher energy density can be obtained. The anode active material layer 22B may exist at the time of assembling, or may not exist at the time of assembling, and may be formed of lithium metal precipitated at the time of charge. Moreover, the anode active material layer 22B may be used also as a current collector, and the anode current collector 22A may be removed.

When the secondary battery is charged, lithium ions are extracted from the cathode 21, and the lithium ions are precipitated on the surface of the anode current collector 22A as lithium metal through the electrolytic solution. When the secondary battery is discharged, the lithium metal is dissolved from the anode active material layer 22B as lithium ions, and the lithium ions are inserted into the cathode 21 through the electrolytic solution.

In the secondary battery, in the case where the capacity of the anode is represented by a capacity component based on precipitation and dissolution of lithium, the ionic compound shown in Chemical Formula 5 as an electrolyte salt is included in the electrolytic solution, so the cycle characteristics can be improved.

(Fourth Battery)

Figure 3:
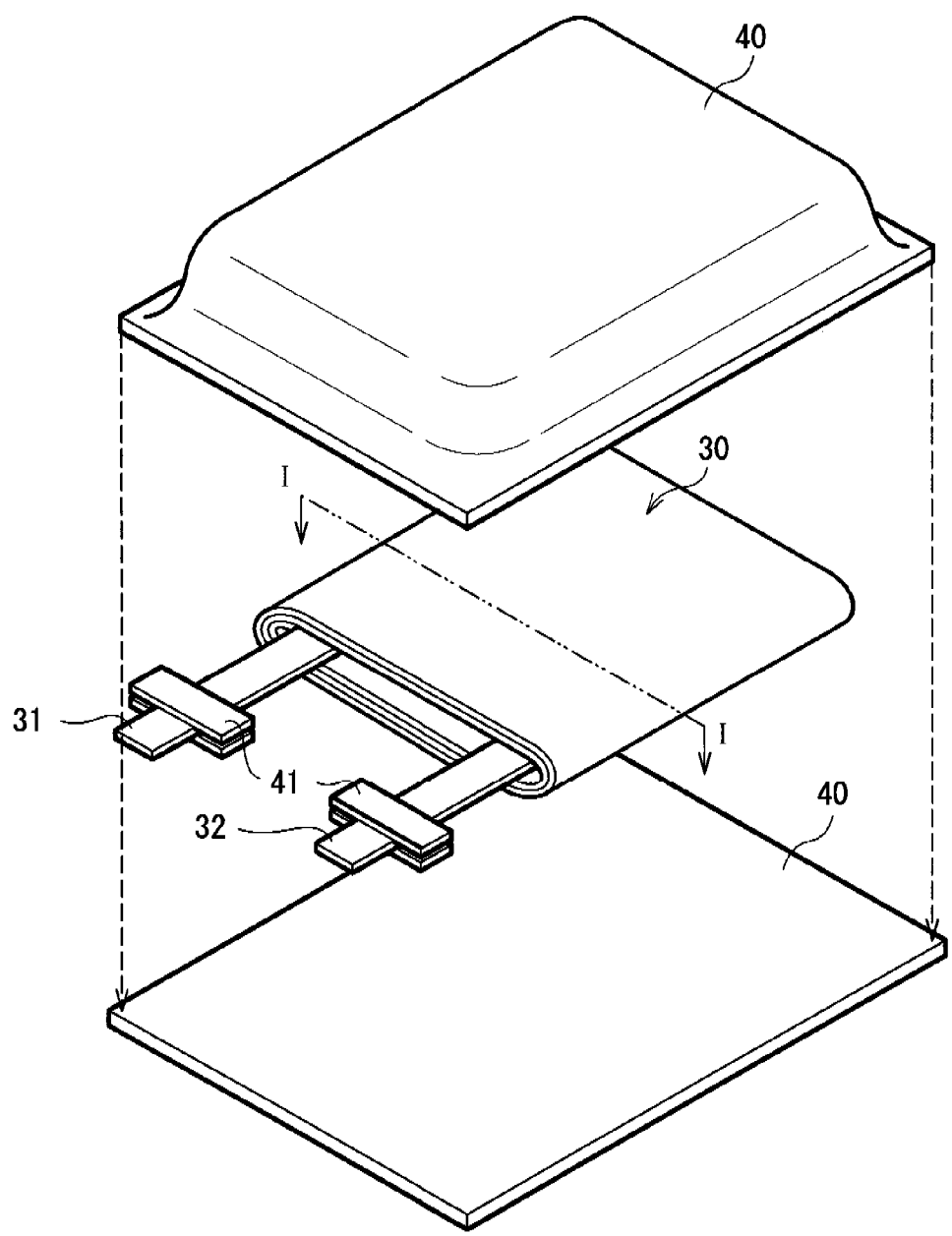
FIG. 3 is an exploded perspective view of a third battery using the ionic compound according to the embodiment of the invention as an electrolyte salt.

FIG. 3 shows an exploded perspective view of a fourth battery. In the battery, a spirally wound electrode body 30 to which a cathode lead 31 and an anode lead 32 are attached is contained in film-shaped package members 40, and the structure of the battery is a so-called laminate film type.

The cathode lead 31 and the anode lead 32 are drawn from the interiors of the package members 40 to outside, for example, in the same direction. The cathode lead 31 and the anode lead 32 are made of, for example, a metal material such as aluminum, copper, nickel or stainless in a sheet shape or a mesh shape.

The package members 40 are made of, for example, a rectangular aluminum laminate film including a nylon film, aluminum foil and a polyethylene film which are bonded in this order. The package members 40 are arranged so that the polyethylene film of each of the package members 40 faces the spirally wound electrode body 30, and edge portions of the package members 40 are adhered to each other by fusion bonding or an adhesive. An adhesive film 41 is inserted between the package members 40 and the cathode lead 31 and the anode lead 32 for preventing the entry of outside air. The adhesive film 41 is made of, for example, a material having adhesion to the cathode lead 31 and the anode lead 32, for example, a polyolefin resin such as polyethylene, polypropylene, modified polyethylene or modified polypropylene.

In addition, the package members 40 may be made of a laminate film with any other structure, a polymer film such as polypropylene or a metal film instead of the above-described three-layer aluminum laminate film.

Figure 4:
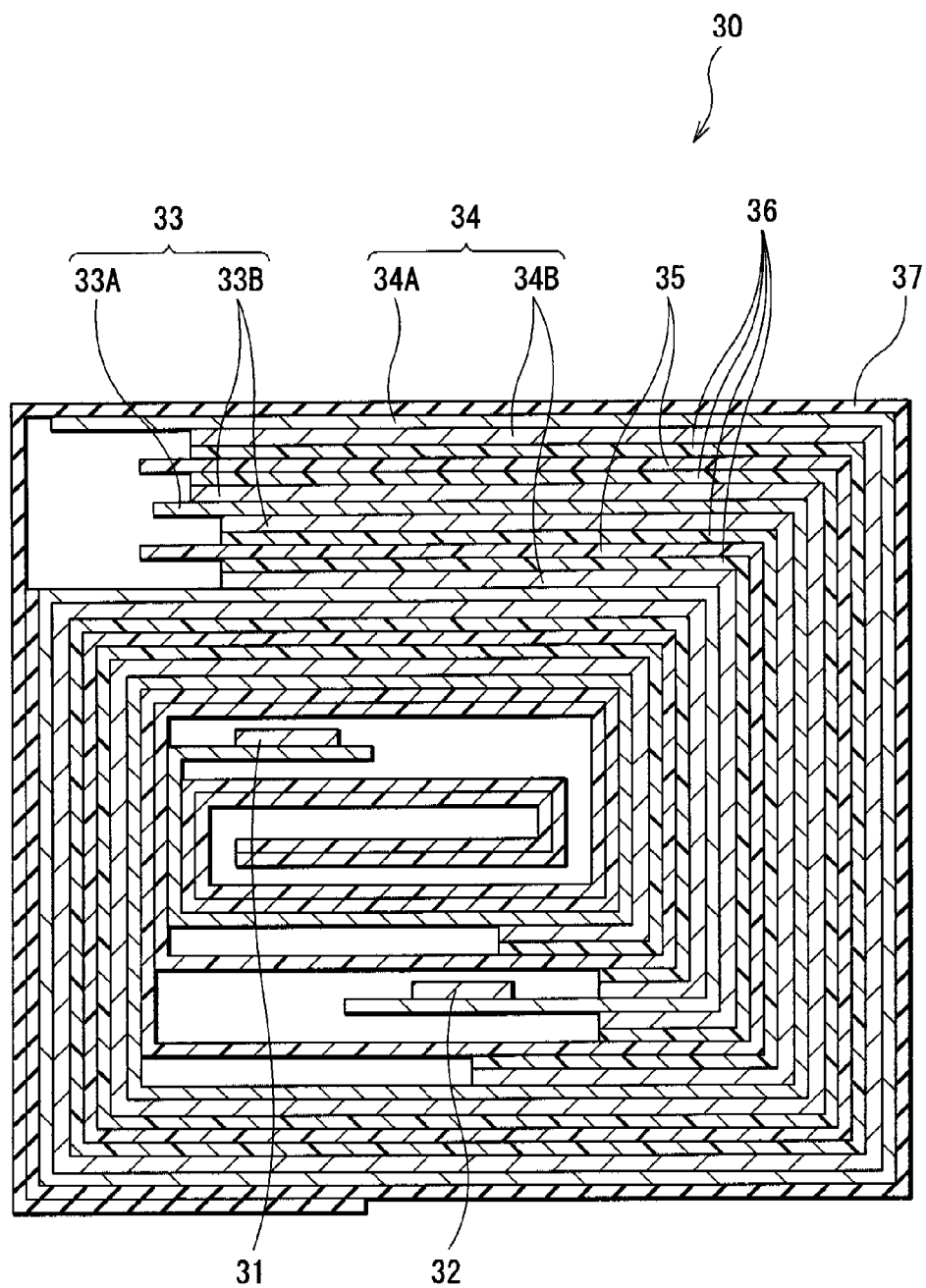
FIG. 4 is a sectional view of a spirally wound electrode body taken along a line I-I of FIG. 3.

FIG. 4 shows a sectional view of the spirally wound electrode body 30 taken along a line I-I of FIG. 3. The spirally wound electrode body 30 is a spirally wound laminate including a cathode 33 and an anode 34 with a separator 35 and an electrolyte layer 36 in between, and an outermost portion of the spirally wound electrode body 30 is protected with a protective tape 37.

The cathode 33 has a structure in which a cathode active material layer 33B is arranged on both sides of a cathode current collector 33A. The anode 34 has a structure in which an anode active material layer 34B is arranged on both sides of an anode current collector 34A, and the anode 34 is arranged so that the anode active material layer 34B faces the cathode active material layer 33B. The structures of the cathode current collector 33A, the cathode active material layer 33B, the anode current collector 34A, the anode active material layer 34B and the separator 35 are the same as those of the cathode current collector 21A, the cathode active material layer 21B, the anode current collector 22A, the anode active material layer 22B and the separator 23 in the above-described first and second batteries, respectively.

The electrolyte layer 36 includes the electrolytic solution including the ionic compound according to the embodiment as the electrolyte salt, and a polymer compound as a holding body which holds the electrolytic solution, and is a so-called gel electrolyte. The gel electrolyte is preferable, because the gel electrolyte can obtain high ionic conductivity (for example, 1 mS/cm or over at room temperature), and can prevent leakage of the battery.

Examples of the polymer compound include polyacrylonitrile, polyvinylidene fluoride, a copolymer of polyvinylidene fluoride and polyhexafluoropyrene, polytetrafluoroethylene, polyhexafluoropropylene, polyethylene oxide, polypropylene oxide, polyphosphazene, polysiloxane, polyvinyl acetate, polyvinyl alcohol, poly(methyl methacrylate), a polyacrylic acid, polymethacrylic acid, styrene-butadiene rubber, nitrile-butadiene rubber, polystyrene, polycarbonate and the like. One kind or a mixture including a plurality of kinds selected from these polymer compounds may be used. In particular, in terms of electrochemical stability, polyacrylonitrile, polyvinylidene fluoride, polyhexafluoropropylene, polyethylene oxide or the like is preferably used. The additive amount of the polymer compound in the electrolytic solution depends on compatibility between them, but is preferably within a range from 5 wt % to 50 wt % inclusive.

The content of the electrolyte salt is the same as that in the above-described first, second and third batteries. The solvent in this case has a wide concept including not only a liquid solvent but also a solvent having ionic conductivity capable of dissociating the electrolyte salt. Therefore, in the case where a polymer compound having ionic conductivity is used, the polymer compound is included in the concept of the solvent.

The secondary battery can be manufactured by the following steps, for example.

At first, the electrolyte layer 36 is formed by applying a precursor solution including the electrolytic solution, the polymer compound and a mixed solvent to the cathode 33 and the anode 34, and volatilizing the mixed solvent. Next, the cathode lead 31 is attached to the cathode current collector 33A, and the anode lead 32 is attached to the anode current collector 34A. Next, after the cathode 33 on which the electrolyte layer 36 is formed and the anode 34 on which the electrolyte layer 36 is formed is laminated with the separator 35 in between to form a laminate, the laminate is spirally wound in a longitudinal direction, and the protective tape 37 is bonded to an outermost portion of the laminate so as to form the spirally wound electrode body 30. After that, for example, the spirally wound electrode body 30 is sandwiched between the package members 40, and edge portions of the package members 40 are adhered to each other by thermal fusion bonding or the like to seal the spirally wound electrode body 30 in the package members 40. At this time, the adhesive film 41 is inserted between the cathode lead 31, the anode lead 32 and the package members 40. Thereby, the secondary battery shown in FIGS. 3 and 4 is completed.

Moreover, the battery may be manufactured by the following steps. At first, after the cathode lead 31 and the anode lead 32 are attached to the cathode 33 and the anode 34, respectively, the cathode 33 and the anode 34 are laminated with the separator 35 in between to form a laminate, and the laminate is spirally wound, and the protective tape 37 is bonded to an outermost portion of the spirally wound laminate so as to form a spirally wound body as a precursor body of the spirally wound electrode body 30. Next, the spirally wound body is sandwiched between the package members 40, and the edge portions of the package members 40 except for one side are adhered by thermal fusion bonding or the like to form a pouched package, thereby the spirally wound body is contained in the package members 40. A component for an electrolyte which includes the electrolytic solution, monomers as materials of a polymer compound and a polymerization initiator and, if necessary, any other material such as a polymerization inhibitor is prepared, and the component is injected in the package members 40, and then an opened portion of the package members 40 are sealed by thermal fusion bonding or the like. After that, the monomers are polymerized by applying heat to form the polymer compound, thereby the gel electrolyte layer 36 is formed. Thus, the secondary battery shown in FIGS. 3 and 4 is completed.

The functions and effects of the secondary battery is the same as those of the above-described first and second secondary batteries.

EXAMPLES

Specific examples of the invention will be described in detail below.

At first, as a representative of the ionic compound according to the embodiment of the invention, fluorotrifluoromethyl [oxalate-O,O'] lithium borate shown in Chemical Formula 6(1) was synthesized by the following steps. At first, 10 g of dimethyl carbonate (DMC)-coordinated fluoro(trifluoromethyl) borate, 4.7 g of an oxalic acid, and 60 ml of DMC were mixed to form a mixture, and while agitating the mixture, 4.9 g of tetrachlorosilane was dripped into the mixture, and then the mixture was agitated on all night to cause reaction. After the reaction, the reactant was decompressed to be concentrated, and then the concentrated reactant was recrystallized with a mixed solvent including DMC and toluene to obtain 6.5 g of a colorless compound.

The compound was identified by nuclear magnetic resonance (NMR) through the use of acetone-$d_6$ as a deuterated solvent. As a result, a 11B-NMR spectrum ($NaBH_4$ basis) was observed at 1.08 ppm (quin.), and 19F-NMR spectra ($CF_3COOH$ basis) were observed at −77.5 ppm (m) and −167.4 ppm (m). As a result, it could be confirmed that the obtained compound was fluorotrifluoromethyl [oxalate-O, O'] lithium borate. Therefore, it was confirmed that the ionic compound according to the embodiment of the invention could be synthesized.

Next, a series of electrolytic solutions were formed by using the ionic compound as the electrolyte salt by the following steps.

Example 1

After ethylene carbonate (EC) and DMC were mixed at a volume ratio of 1:1 to form a mixture, fluorotrifluoromethyl [oxalate-O,O'] lithium borate was dissolved in the mixture as the electrolyte salt. At that time, the concentration of the electrolyte salt was 1 mol/$dm^3$.

Comparative Example 1-1

An electrolytic solution was formed by the same steps as those in Example 1, except that instead of fluorotrifluoromethyl[oxalate-O,O']lithium borate, bis[oxalate-O,O'] lithium borate was used as the electrolyte salt.

Comparative Example 1-2

An electrolytic solution was formed by the same steps as those in Example 1, except that instead of fluorotrifluoromethyl[oxalate-O,O']lithium borate, difluoro[oxalate-O,O'] lithium borate was used as the electrolyte salt.

When the conductivity (mS/cm) at 25° C. of each of the electrolytic solutions of Example 1 and Comparative Examples 1-1 and 1-2 was measured with an AC bipolar cell, the results shown in Table 1 were obtained.

TABLE 1

|  | ELECTROLYTE SALT | CONDUCTIVITY (mS/cm) |
|---|---|---|
| EXAMPLE 1 | Fluorotrifluoromethyl [oxalate-O,O'] lithium borate | 9.18 |
| COMPARATIVE EXAMPLE 1-1 | bis[oxalate-O,O'] lithium borate | 5.47 |
| COMPARATIVE EXAMPLE 1-2 | difluoro[oxalate-O,O'] lithium borate | 8.72 |

As shown in Table 1, the conductivities of the electrolytic solutions were 9.18 mS/cm, 5.47 mS/cm and 8.72 mS/cm in Example 1 and Comparative Examples 1-1 and 1-2, respectively. In other words, compared to Comparative Examples 1-1 including bis[oxalate-O,O'] lithium borate with a symmetric structure and Comparative Example 1-2 including difluoro[oxalate-O,O'] lithium borate with a symmetric structure, the conductivity was higher in Example 1 including fluorotrifluoromethyl[oxalate-O,O'] lithium borate with an asymmetric structure. Therefore, it was confirmed that when the electrolytic solution included an ionic compound having the structure shown in Chemical Formula 5 as the electrolyte salt, the conductivity was improved.

Next, as a series of secondary batteries using the electrolytic solutions, cylindrical type secondary batteries shown in FIGS. 1 and 2 were formed.

Example 2

At first, the anode 22 was formed. More specifically, 50 parts by weight of petroleum pitch as a binder was added to 100 parts by weight of coal coke as a filler, and they were mixed at 100° C. to form a mixture, and then the mixture was compression molded by pressing to obtain a precursor body of a carbon molding body. Next, the precursor body was heated at 1000° C. or less to obtain the carbon molding body. Then, after the carbon molding body was impregnated with binder pitch molten at 200° C. or less, a pitch impregnation/firing process in which a heat treatment was performed at 1000° C. was repeated a few times. Next, the carbon molding body was heated at a maximum temperature of 3000° C. in an inert atmosphere to obtain a graphitized molding body. Then, the graphitized molding body was pulverized to obtain a powdery anode active material.

Next, 90 parts by weight of graphite powder as an anode active material and 10 parts by weight of polyvinylidene fluoride (PVDF) as a binder were mixed to form an anode mixture, and then the anode mixture was dispersed in N-methyl-2-pyrrolidone as a solvent to form paste-form anode mixture slurry. Next, the anode mixture slurry was applied to both sides of the anode current collector 22A made of strip-shaped copper foil, and the anode mixture slurry was dried and compression molded, thereby the anode active material layer 22B was formed. At that time, the area density of the anode active material layer 22B was 25 mg/cm$^2$. Finally, the anode lead 26 made of nickel was attached to an end of the anode current collector 22A by welding.

Next, the cathode 21 was formed. More specifically, lithium carbonate ($Li_2CO_3$) and cobalt carbonate ($CoCO_3$) were mixed at a molar ratio of 0.5:1, and the mixture was fired in air at 900° C. for 5 hours to obtain lithium cobalt complex oxide ($LiCoO_2$). When the X-ray diffraction was conducted on the obtained lithium cobalt complex oxide, the diffraction pattern of the obtained $LiCoO_2$ closely matched a peak of $LiCoO_2$ listed in the JCPDS (Joint Committee of Powder Diffraction Standard) file. Next, the lithium cobalt complex oxide was pulverized to obtain a powdery cathode active material. At that time, the accumulative 50% diameter obtained by a laser diffraction method was 15 μm.

Next, 95 parts by weight of $LiCoO_2$ and 5 parts by weight of $Li_2CO_3$ were mixed to form a mixture, and 91 parts by weight of the mixture as the cathode active material, 6 parts by weight of graphite as an electrical conductor and 3 parts by weight of polyvinylidene fluoride as a binder were mixed to prepare a cathode mixture, and then the cathode mixture was dispersed in N-methyl-2-pyrrolidone as a solvent to form paste-form cathode mixture slurry. Next, after the cathode mixture slurry was applied to both sides of the cathode current collector 21A made of strip-shaped aluminum foil with a thickness of 20 μm, and the cathode mixture slurry was dried and compression molded, thereby the cathode active material layer 21B was formed. At that time, the area density of the cathode active material layer 21B was 55 mg/cm$^2$. Finally, the cathode lead 25 made of aluminum was attached to an end of the cathode current collector 21A by welding.

Next, the anode 22, the separator 23 made of a microporous polypropylene film with a thickness of 25 μm and the cathode 21 were laminated in this order to form a laminate, and the laminate was spirally wound several times, and an outermost part was fixed by an adhesive tape to form the spirally wound electrode body 20 with an outside diameter of 18 mm. Next, after the battery can 11 made of nickel-plated iron was prepared, the spirally wound electrode body 20 was sandwiched between a pair of insulating plates 12 and 13, and the anode lead 26 was welded to the battery can 11, and the cathode lead 25 was welded to the safety valve mechanism 15, thereby the spirally wound electrode body 20 was contained in the battery can 11. Next, the electrolytic solution of Example 1 was injected into the battery can 11 by a decompression method. Then, the safety valve mechanism 15, the PTC device 16 and the battery cover 14 were fixed by caulking the battery can 11 by the gasket 17 of which the surface is coated with asphalt. Thereby, the hermeticity of the battery can 11 was secured, and a cylindrical type secondary battery with a diameter of 18 mm and a height of 65 mm was completed.

Comparative Example 2-1

An electrolytic solution was prepared by the same steps as those in Example 1, except that instead of fluorotrifluoromethyl[oxalate-O,O']lithium borate, $LiPF_6$ was used as the electrolyte salt, and a secondary battery using the electrolytic solution was formed by the same steps as those in Example 2.

Comparative Example 2-2

A secondary battery was formed by the same steps as those in Example 2, except that instead of the electrolytic solution of Example 1, the electrolytic solution of Comparative Example 1-2 was used.

When the cycle characteristics of the secondary batteries of Example 2 and Comparative Examples 2-1 and 2-2 were determined, the results shown in Table 2 were obtained. To determine the cycle characteristics, a charge-discharge cycle was repeated 100 times, and as the cycle characteristics, the discharge capacity retention ratio in the 100th cycle to the discharge capacity in the first cycle, that is, the discharge capacity retention ratio (%)=(discharge capacity in the 100th cycle/initial discharge capacity)×100(%) was determined. At that time, as the conditions of one charge-discharge cycle, after the secondary batteries were charged at a first charge current of 2.75 A (1.25 C) until the charge voltage reached 4.1 V, the secondary batteries were charged at a second charge current of 1.1 A (0.5 C) until reaching a maximum charge voltage 4.2 V, and secondary batteries were charged at a constant voltage of 4.2 V, and then the charge was completed at a current of 20 mA, and after that, the secondary batteries were discharged at a current 2 A until reaching 3.0 V.

TABLE 2

| | ELECTROLYTE SALT | DISCHARGE CAPACITY RETENTION RATIO (%) |
|---|---|---|
| EXAMPLE 2 | Fluorotrifluoromethyl [oxalate-O,O'] lithium borate | 88 |
| COMPARATIVE EXAMPLE 2-1 | $LiPF_6$ | 85 |
| COMPARATIVE EXAMPLE 2-2 | difluoro[oxalate-O,O'] lithium borate | 83 |

As shown in Table 2, the discharge capacity retention ration of the secondary batteries of Example 2 and Comparative Examples 2-1 and 2-2 are 88%, 85% and 83%, respectively. In other words, the discharge capacity retention ratio in Example 2 including fluorotrifluoromethyl[oxalate-O,O'] lithium borate was higher than those in Comparative Examples 2-1 and 2-2 including $LiPF_6$ and difluoro[oxalate-O,O'] lithium borate, respectively. Therefore, in the secondary battery according to the embodiment of the invention, it was confirmed that when the electrolytic solution included the ionic compound having the structure shown in Chemical Formula 5 as the electrolyte salt, the cycle characteristics could be improved.

Although the present invention is described referring to the embodiment and the examples, the invention is not limited to them, and can be variously modified. For example, the ionic compound according to the embodiment of the invention is applied to not only the above-described application but also any other application. Examples of the other application include a catalyst for synthesis and the like.

Moreover, in the above-described embodiment and the above-described examples, the case where the electrolyte solution or the gel electrolyte in which the polymer compound holds the electrolytic solution is used as the electrolyte of the secondary battery according to the embodiment of the invention is described; however, any other electrolyte may be used. Examples of the electrolyte include a mixture of an ionic conducting inorganic compound such as ionic conducting ceramic, ionic conducting glass or ionic crystal and an electrolytic solution, a mixture of another inorganic compound and an electrolytic solution, a mixture of the inorganic compound and a gel electrolyte and the like.

Further, in the above-described embodiment and the above-described examples, the lithium-ion secondary battery in which the capacity of the anode is represented by a capacity component based on the insertion and extraction of lithium, or the lithium metal secondary battery in which lithium metal is used as the anode active material, and the capacity of the anode is represented by a capacity component based on the precipitation and dissolution of lithium is described as the secondary battery according to the embodiment of the invention; however, the invention is not necessarily limited to them. The invention is applicable to a secondary battery in which the capacity of the anode includes a capacity component based on insertion and extraction of lithium and a capacity component based on precipitation and dissolution of lithium by reducing the charge capacity of an anode material capable of inserting and extracting lithium to smaller than the discharge capacity of a cathode, and the capacity of the anode is represented by the sum of the capacity components in the same manner.

In the embodiments and the examples, the cylindrical type secondary battery and the laminate film type secondary battery are described; however, the invention is applicable to a secondary battery with any other shape such as a coin type, a button type or a prismatic type or a secondary battery with any other structure such as a laminate structure. In addition, the invention is applicable to not only the secondary batteries but also any other batteries such as primary batteries.

It should be understood by those skilled in the art that various modifications, combinations, sub-combinations and alterations may occur depending on design requirements and other factors insofar as they are within the scope of the appended claims or the equivalents thereof.

What is claimed is:

1. An ionic compound comprising:
a structure shown in Chemical Formula 1:

[Chemical Formula 1]

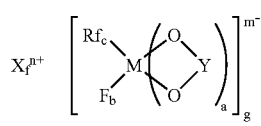

where $X^{n+}$ represents an ion of a Group 1A element or a Group 2A element in the short form of the periodic table of the elements, or an onium ion, M represents a transition metal, or a Group 3B element, a Group 4B element or a Group 5B element in the short form of the periodic table of the elements, Rf represents a fluorinated alkyl group or a fluorinated aryl group having a carbon number of 1 to 10, and Y represents $ZC(CR_2)_dCZ$, $O_2S(CR_2)_eSO_2$ or $OC(CR_2)_eSO_2$ (Z represents =O, a halogenated alkyl group or a halogen group, R represents a hydrogen group, an alkyl group, a halogenated alkyl group or a halogen group), and a, g and n each are an integer of 1 or 2, b, c and e each are an integer of 1 to 4, d is 0 or an integer of 1 to 4, and f and m each are an integer of 1 to 3.

2. The ionic compound according to claim 1, wherein the ionic compound includes fluorotrifluoromethyl[oxalate-O,O'] lithium borate.

3. An electrolytic solution comprising:
a solvent; and
an electrolyte salt shown in Chemical Formula 2:

[Chemical Formula 2]

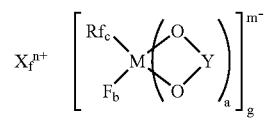

where $X^{n+}$ represents an ion of a Group 1A element or a Group 2A element in the short form of the periodic table of the elements, or an onium ion, M represents a transition metal, or a Group 3B element, a Group 4B element or a Group 5B element in the short form of the periodic table of the elements, Rf represents a fluorinated alkyl group or a fluorinated aryl group having a carbon number of 1 to 10, and Y represents $ZC(CR_2)_dCZ$, $O_2S(CR_2)_eSO_2$ or $OC(CR_2)_eSO_2$ (Z represents =O, a halogenated alkyl group or a halogen group, R represents a hydrogen group, an alkyl group, a halogenated alkyl group or a halogen group), and a, g and n each are an integer of 1 or 2, b, c and e each are an integer of 1 to 4, d is 0 or an integer of 1 to 4, and f and m each are an integer of 1 to 3.

4. An electrochemical device comprising:
an electrolytic solution including an electrolyte salt shown in Chemical Formula 3:

[Chemical Formula 3]

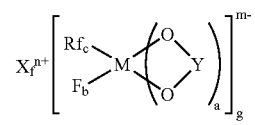

where $X^{n+}$ represents an ion of a Group 1A element or a Group 2A element in the short form of the periodic table of the elements, or an onium ion, M represents a transition metal, or a Group 3B element, a Group 4B element or a Group 5B element in the short form of the periodic table of the elements, Rf represents a fluorinated alkyl group or a fluorinated aryl group having a carbon number of 1 to 10, and Y represents $ZC(CR_2)_dCZ$, $O_2S(CR_2)_eSO_2$ or $OC(CR_2)_eSO_2$ (Z represents =O, a halogenated alkyl group or a halogen group, R represents a hydrogen group, an alkyl group, a halogenated alkyl group or a halogen group), and a, g and n each are an integer of 1 or 2, b, c and e each are an integer of 1 to 4, d is 0 or an integer of 1 to 4, and f and m each are an integer of 1 to 3.

5. A battery comprising a cathode, an anode and an electrolytic solution, wherein
the electrolytic solution includes an electrolyte salt shown in Chemical Formula 4:

[Chemical Formula 4]

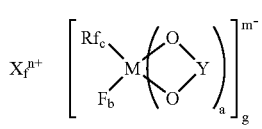

where $X^{n+}$ represents an ion of a Group 1A element or a Group 2A element in the short form of the periodic table of the elements, or an onium ion, M represents a transition metal, or a Group 3B element, a Group 4B element or a Group 5B element in the short form of the periodic table of the elements, Rf represents a fluorinated alkyl group or a fluorinated aryl group having a carbon number of 1 to 10, and Y represents $ZC(CR_2)_dCZ$, $O_2S(CR_2)_eSO_2$ or $OC(CR_2)_eSO_2$ (Z represents $=$O, a halogenated alkyl group or a halogen group, R represents a hydrogen group, an alkyl group, a halogenated alkyl group or a halogen group), and a, g and n each are an integer of 1 or 2, b, c and e each are an integer of 1 to 4, d is 0 or an integer of 1 to 4, and f and m each are an integer of 1 to 3.

* * * * *